United States Patent
Hoopes

(10) Patent No.: US 6,940,004 B2
(45) Date of Patent: Sep. 6, 2005

(54) POTATO CULTIVAR FL 2027

(75) Inventor: Robert W. Hoopes, Rhinelander, WI (US)

(73) Assignee: Frito-Lay North America, Inc., Plano, TX (US)

( * ) Notice: Subject to any disclaimer, the term of this patent is extended or adjusted under 35 U.S.C. 154(b) by 0 days.

(21) Appl. No.: 10/681,607

(22) Filed: Oct. 8, 2003

(65) Prior Publication Data

US 2005/0081269 A1 Apr. 14, 2005

(51) Int. Cl.$^7$ ............... A01H 5/00; A01H 5/06; A01H 1/00; A01H 1/02; C12N 5/04
(52) U.S. Cl. ............... 800/317.2; 800/260; 800/263; 800/265; 800/266; 800/268; 800/278; 800/279; 800/284; 800/300; 800/302; 435/417; 435/418; 435/421; 435/429; 435/430; 435/430.1; 435/468
(58) Field of Search ............... 800/260, 263, 800/265, 266, 268, 269, 277, 278, 279, 284, 287, 317.2, 300, 302; 435/417, 418, 421, 429, 430, 430.1, 468, 469, 470

(56) References Cited

U.S. PATENT DOCUMENTS 5,523,520 A * 6/1996 Hunsperger et al. ........ 800/260

OTHER PUBLICATIONS

Kraft et al. Theor. Appl. Genet. 101:323–326 (2000).*
Eshed et al. Genetics 143:1807–1817 (1996).*
Visker et al. Theor. Appl. Genet. 106:317–325 (2003).*
Thill et al. Euphytica 84:73–80 (1995).*

* cited by examiner

Primary Examiner—David T. Fox
Assistant Examiner—Keith O. Robinson
(74) Attorney, Agent, or Firm—Jondle & Associates P.C.

(57) ABSTRACT

A novel potato cultivar of the genus and species *Solanum tuberosum*, designated FL 2027, is disclosed. The invention relates to the tubers of potato variety FL 2027, to the plants of potato variety FL 2027, to the seeds of potato variety and to methods for producing hybrid potato variety. The invention further relates to potato variety tubers, seeds and plants produced by crossing the potato variety FL 2027 with another potato plant, and to Single Gene Converted plants.

19 Claims, No Drawings

POTATO CULTIVAR FL 2027

BACKGROUND OF THE INVENTION

The present invention relates to a novel potato variety and to the tubers, plants, plant parts, tissue culture and seeds produced by that potato variety.

The publications and other materials used herein to illuminate the background of the invention and, in particular cases, to provide additional details respecting the practice, are incorporated by reference and for convenience, are referenced in the following text by author and date and are listed alphabetically by author in the appended bibliography.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through crossbreeding of potatoes, researchers hope to obtain potatoes with the desirable characteristics of good processability, high solids content, high yield, resistance to diseases and pests and adaptability to various growing areas and conditions.

The U.S. acreage planted in potatoes has declined since the 1960s and 1970s, and this decline, coupled with increasing consumption, must be offset by higher useable yields. In some areas, diseases and pests damage crops despite the use of herbicides and pesticides. The problem of the golden nematode in the United States, presently endemic to portions of New York State, is one example of the destruction to susceptible potato varieties. Potato varieties with high yields, disease resistance and adaptability to new environments can eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement. Potato varieties in the warm southern tier of states are most in need of solids improvement overall, while those varieties grown and stored in the colder northern tier of states are most in need of the ability to recondition after cool or cold storage to increase their value for use in the potato chip industry. Reconditioning is necessary to elevate the temperature of the potatoes after cold storage and before further processing.

The research leading to potato varieties which combine the advantageous characteristics referred to above is largely empirical. This research requires large investments of time, manpower, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses, and tubers are harvested and retained from thousands of individual seedlings. The next year a single tuber from each resulting seedling is planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

Long-term, controlled-environment storage has been a feature of the northern, principal producing areas for many years. Potatoes harvested by October must be kept in good condition for up to eight months in temperatures that may drop to −30 degrees C. at times and with very low relative humidity in the outside air. Storages are well insulated, not only to prevent heat loss but also to prevent condensation on outside walls. The circulation of air at the required temperature and humidity is automatically controlled depending on the purpose for which the potatoes are being stored. Sprout inhibition is now largely carried out in storage as it has been found to be more satisfactory than the application of maleic hydrazide (MH30) in the field.

Proper testing of new plants should detect any major faults and establish the level of superiority or improvement over current varieties. In addition to showing superior performance, a new variety must be compatible with industry standards or create a new market. The introduction of a new variety will increase costs of the tuber propagator, the grower, processor and consumer; for special advertising and marketing, altered tuber propagation and new product utilization. The testing preceding release of a new variety should take into consideration research and development costs as well as technical superiority of the final variety. Once the varieties that give the best performance have been identified, the tuber can be propagated indefinitely as long as the homogeneity of the variety parent is maintained.

For tuber propagated varieties, it must be feasible to produce, store and process potatoes easily and economically.

Thus, there is a continuing need to develop potato cultivars which provide good processability out of storage, with minimal bruising, for manufacturers of potato chips and other potato products and to combine this characteristic with the properties of disease resistance, resistance to pests. The present invention addresses this need by providing the new variety as described herein.

SUMMARY OF THE INVENTION

According to the invention, there is provided a novel potato cultivar of the genus and species, *Solanum*

*tuberosum*, designated FL 2027. This invention thus relates to the tubers of potato variety FL 2027, the plants and plant parts of potato variety FL 2027 and to methods for producing a potato plant produced by crossing the potato variety FL 2027 with itself or another potato variety. This invention further relates to hybrid potato seeds and plants produced by crossing the potato variety FL 2027 with another potato plant.

In another aspect, the present invention provides for Single Gene Converted plants of FL 2027. The single gene transferred may be a dominant or recessive allele. Preferably, the single gene transferred will confer such traits as herbicide resistance, insect resistance, resistance for bacterial, fungal or viral disease, uniformity and increase in concentration of starch and other carbohydrates, decrease in tendency of tuber to bruise and decrease in the rate of conversion of starch to sugars. The single gene transferred may be a naturally occurring gene or a transgene introduced through genetic engineering techniques.

DEFINITIONS

In the description and tables which follow, a number of terms are used. In order to provide a clear and consistent understanding of the specification and claims, including the scope to be given such terms, the following definitions are provided:

FL Solids. Percentage of solid matter contained in tubers. FL Solids=(178.093×Specific Gravity)−175.560.

Solid/Acre. Marketable yield (in pounds)×FL Solids.

Total Yield. Total weight of all harvested tubers.

Marketable Yield. Weight of all tubers harvested that are between 2 and 4 inches in diameter; Measured in cwt (hundred weight)

cwt=100 pounds

Vine Maturity. Plants ability to continue to utilize carbohydrates and photosynthesize. Scale of 1 to 5.1=dead vines 5=vines green, still flowering.

DETAILED DESCRIPTION OF THE INVENTION

A novel potato cultivar of the present invention, which has been designated FL 2027, has been obtained by selectively crossbreeding parental clones through several generations. These parents were selected as breeding parents because of their high yields, excellent chip color off the field and out of storage, and resistance to hollow heart.

FL 2027 has early to mid-season chipping variety with light yellow fleshed compressed tubers. FL 2027 has outstanding attributes that contribute to excellent chip appearance, and good flavor.

The chip appearance, manufacturing efficiency and consumer acceptability have been equal or superior to checks.

FL 2027 has been uniform and stable since its origin as a single plant in 1995. No variants of FL 2027 have been observed.

As a chipping variety for fresh use from early to mid season harvests and use out of storage, FL 2027 is most similar to Atlantic. FL 2027 can be distinguished from Atlantic with regard to the following traits: FL 2027 tubers have light grayed-yellow skin (RHS162D) and evenly distributed eyes, Atlantic has brown skin (RHS 199B) and predominantly apical eyes. FL 2027 has smaller leaf stipules and a higher average number of leaflet pairs than Atlantic. It also has a pentagonal corolla and no color in the calyx, while Atlantic has a rotate corolla and medium color in its calyx. The sprouts of FL 2027 tend to be spherical in shape and pale blue violet in color. Atlantic's sprouts are more conical in shape and very dark blue violet in color.

In addition to the morphological characteristics and disease and pest resistance as described above, the plants of this invention are characterized by their protein "fingerprint" patterns. The protein "fingerprint" is determined by separating tuber proteins on an electrophoretic gel under certain defined conditions. The pattern of the proteins, attributable to their differential mobilities on the electrophoretic gel, have been found to be characteristic of the particular plant involved. This pattern has thus been termed a "fingerprint." Isozyme fingerprints of all available North American potato varieties have revealed that no two varieties have the same pattern for the enzymes tested. (Douches and Ludlam, 1991). The isozyme fingerprint of FL 2027 has been established as distinct from that of any other variety tested, including Atlantic (Douches and Ludlam, 1991). These techniques generally involve extracting proteins from the tuber and separating them electrophoretically.

Potato variety FL 2027 has the following morphologic and other characteristics.

| | |
|---|---|
| Classification: | Solanum Tuberosum L. |
| Plant characteristics: | |
| (Observed at beginning of bloom) | |
| Growth habit: | Semi-erect (30–45° with ground) |
| Type: | Intermediate |
| Maturity: | 110–120 days after planting (DAP) at vine senescence |
| Planting Date: | Mar. 1, 2002 |
| Region Area: | Charleston, MO |
| Maturity Class: | Early to Mid-season |
| Stem Characteristics: | |
| (Observed at early first bloom) | |
| Stem (anthocyanin coloration): | Absent |
| Stem (wings): | Weak |
| Leaf Characteristics: (Observed fully developed leaves located in the middle one-third of plant): | |
| Leaf (color): | Medium green - RHS 146A |
| Leaf (pubescence density): | Sparse to Medium |
| Leaf (pubescence length) | Medium |
| Leaf (silhouette): | Open |
| Leaf stipules (size): | Small |
| Petioles (anthocyanin coloration): | Absent |
| Terminal leaflet (shape): | Medium/ovate |
| Terminal leaflet (shape of tip): | Acuminate |
| Terminal leaflet (shape of base): | Truncate |
| Terminal leaflet (margin waviness): | Medium |
| Primary leaflets (average pairs): | 5 |
| Primary leaflets (shape of tip): | Acuminate |
| Primary leaflets (size): | Medium |
| Primary leaflets (shape): | Medium ovate |
| Primary leaflets (shape of base): | Cordate to Truncate |
| Number of leaflets (secondary and tertiary): | 6 |
| Inflorescence Characteristics: | |
| Number of inflorescence/plant: | 8.5 |
| Number of florets/inflorescence: | 13.4 |
| Corolla (shape): | Pentagonal |
| Corolla (inner surface color): | White - 155A RHS |
| Corolla (outer surface color): | Violet - 84D RHS (fades to white quickly) |
| Calyx (anthocyanin coloration): | Absent |
| Anthers (color): | Yellow/Orange - 14A RHS |
| Anthers (shape): | Broad cone |

-continued

| | |
|---|---|
| Pollen (production): | Sparse |
| Stigma (shape): | Capitate |
| Stigma (color): | Yellow/Green - 146A RHS |
| Berry (production): | Low |
| Tuber Characteristics: | |
| Skin (predominant color): | Light yellow - 162D RHS |
| Skin (secondary color): | Absent |
| Skin (texture): | Smooth to Rough |
| Tuber (shape): | Compressed |
| Tuber (thickness): | Slightly flattened |
| Tuber length (mm): | 70.2 |
| Tuber width (mm): | 50.2 |
| Tuber thickness (mm): | 31.5 |
| Tuber eyes (depth): | Intermediate |
| Tuber eyes (lateral): | Shallow |
| Tuber eyes (number): | 10.5 |
| Tuber eyes (distribution): | Evenly distributed |
| Tuber (primary flesh color): | Greyed yellow 160D RHS |
| Tuber (prominence of eyebrows): | Slight prominence | single gene of the recurrent variety is modified, substituted or supplemented with the desired gene from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In Molecular Form and

| | FL 2027 | | | | | Atlantic | | | | |
|---|---|---|---|---|---|---|---|---|---|---|
| Trial for 2001 | FL Solids | Solids/ Acre | Total Yield | Mrkt Yield | Vine Maturity | FL Solids | Solids/ Acre | Total Yield | Mrkt Yield | Vine Maturity |
| Rhinelander Trial (early) | 17.3 | 3062 | 258 | 177 | 4 | 18.2 | 3640 | 252 | 200 | 2 |
| Rhinelander Trial (mid) | 17.5 | 5180 | 321 | 296 | 3 | 18.2 | 5808 | 373 | 309 | 3 |
| E. Nebraska Trial | 16.8 | 3814 | 287 | 227 | 3 | 17.5 | 3780 | 257 | 216 | 4 |

Persons of ordinary skill in the art will recognize that when the term potato plant is used in the context of the present invention, this also includes derivative varieties that retain the essential distinguishing characteristics of FL 2027, such as a Single Gene Converted plant of that variety or a transgenic derivative having one or more value-added genes incorporated therein (such as herbicide or pest resistance. Backcrossing methods can be used with the present invention to improve or introduce a characteristic into the variety. The term backcrossing as used herein refers to the repeated crossing of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene transferred from the nonrecurrent parent.

The selection of a suitable recurrent parent is an important step for a successful backcrossing procedure. The goal of a backcross protocol is to alter or substitute a single trait or characteristic in the original variety. To accomplish this, a Function of the plant Genome, L van Vloten-Doting, (ed.), Plenum Press, New York; Huttner, S. L., et al., 1992, Revising Oversight of Genetically Modified Plants. *Bio/Technology*; Klee, H., et al., 1989, Plant Gene Vectors and Genetic Transformation: Plant Transformation Systems Based on the use of *Agrobacterium tumefaciens, Cell Culture and Somatic Cell Genetics of Plants*; Koncz, C., et al.,1986, The Promoter of $T_L$-DNA Gene 5 Controls the Tissue-Specific Expression of Chimeric Genes Carried by a Novel Type of *Agrobacterium* Binary Vector; *Molecular and General Genetics*; Lawson, C., et al., 1990, Engineering Resistance to Mixed Virus Infection in a Commercial Potato Cultivar: Resistance to Potato Viruses X and Potato Virus Y in Transgenic Russet Burbank, *Bio/Technology*, Mitsky, T. A., et al., 1996, Plants Resistant to Infection by PLRV. U.S. Pat. No. 5,510,253; Newell, C. A., et al.,1991, *Agrobacterium*-mediated transformation of *Solanum tuberosum* L. Cv. Russet Burbank, *Plant Cell Reports*; Perlak, F. J., et al., 1993, Genetically Improved Potatoes: Protection from Damage by Colorado Potato Beetles, *Plant Molecular Biology*, all of which are specifically incorporated herein by reference.

Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these single gene traits are described in U.S. Pat. No. 5,500,365, U.S. Pat. No. 5,387,756, U.S. Pat. No. 5,789,657, U.S. Pat. No. 5,503,999, U.S. Pat. No. 5,589,612, U.S. Pat. No. 5,510,253, U.S. Pat. No. 5,304,730, U.S. Pat. No. 5,382,429, U.S. Pat. No. 5,503,999, U.S. Pat. No. 5,648,249, U.S. Pat. No. 5,312,912, U.S. Pat. No. 5,498,533, U.S. Pat. No. 5,276,268, U.S. Pat. No. 4,900,676, U.S. Pat. No. 5,633,434 and U.S. Pat. No. 4,970,168, the disclosures of which are specifically hereby incorporated by reference.

DEPOSIT INFORMATION

A tuber deposit of the Frito-Lay North America, Inc. proprietary Potato Cultivar FL 2027, disclosed above and recited in the appended claims has been made with the American Type Culture Collection (ATCC), 10801 University Boulevard, Manassas, Virginia 20110. The date of deposit was Sept. 14, 2004. The deposit of 25 vials of tubers was taken from the same deposit maintained by Frito-Lay North America, Inc., since prior to the filing date of this application. All restrictions upon the deposit have been removed, and the deposit is intended to meet all of the requirements of 37 C.F.R. §1.801–1.809. The ATCC accession number is PTA-6212. The deposit will be maintained in the depository for a period of 30 years, or 5 years after the last request, or for the effective life of the patent, whichever is longer, and will be replaced as necessary during that period.

Hereinabove has been set out a new variety of potato, *Solanum tuberosum*, designated as FL 2027, including its physical characteristics and qualities by way of illustration and example for purposes of clarity and understanding. It will be obvious that variations are possible within the scope of this invention, as limited only by the scope of the appended claims.

What is claimed is:

1. A tuber, or part of a tuber, of potato cultivar FL 2027, wherein a representative sample of tubers has been deposited under ATCC Accession No. PTA-6212.

2. A potato plant, or a part thereof, produced by growing the tuber, or a part of the tuber, of claim 1.

3. Pollen of the plant of claim 2.

4. An ovule of the plant of claim 2.

5. A potato plant having all of the physiological and morphological characteristics of the plant of claim 2.

6. A tissue culture of the plant of claim 2.

7. A potato plant regenerated from the tissue culture of claim 6, wherein said plant has all of the physiological and morphological characteristics of the potato plant grown from potato tuber FL 2027.

8. A method for producing a hybrid potato seed wherein the method comprises crossing a first parent potato plant with a second parent potato plant and harvesting the resultant hybrid potato seed, wherein said first parent potato plant or second parent potato plant or both said first potato plant and second potato plant is the potato plant of claim 2.

9. A method for producing a hybrid potato seed wherein the method comprises crossing a first parent potato plant with a second parent potato plant and harvesting the resultant hybrid potato seed, wherein said first parent potato plant or second parent potato plant is the potato plant of claim 2.

10. A method for producing a potato plant that contains in its genetic material one or more transgenes wherein the method comprises crossing the potato plant of claim 2 with either a second plant of another potato variety which contains a transgene, or a transformed potato plant of the potato variety FL 2027, so that the genetic material of the progeny that result from the cross contains the transgene(s) operably linked to a regulatory element.

11. Potato plants, or parts thereof, produced by the method of claim 10.

12. A method of producing an herbicide resistant potato plant wherein the method comprises transforming the potato plant of claim 2 with a transgene that confers herbicide resistance.

13. An herbicide resistant potato plant produced by the method of claim 12.

14. A method of producing an insect resistant potato plant wherein the method comprises transforming the potato plant of claim 2 with a transgene that confers insect resistance.

15. An insect resistant potato plant produced by the method of claim 14.

16. A method of producing a disease resistant potato plant wherein the method comprises transforming the potato plant of claim 2 with a transgene that confers disease resistance.

17. A disease resistant potato plant produced by the method of claim 16.

18. A method of producing a potato plant with modified carbohydrate metabolism wherein the method comprises transforming the potato plant of claim 2 with one or more transgenes encoding an enzyme selected from the group consisting of phosphofructokinase, α-amylase and ADP-glucose pyrophosphorylase or with a transgene encoding an antisense α-amylase mRNA.

19. A potato plant with modified carbohydrate metabolism produced by the method of claim 18.

* * * * *